United States Patent [19]

Krenitsky et al.

[11] 4,347,315

[45] Aug. 31, 1982

[54] SYNTHESIS OF RIBOSIDES USING BACTERIAL PHOSPHORYLASE

[75] Inventors: Thomas A. Krenitsky, Chapel Hill; Janet L. Rideout, Raleigh, both of N.C.

[73] Assignee: Burroughs Wellcome Co., Research Triangle Park, N.C.

[21] Appl. No.: 143,832

[22] Filed: Apr. 25, 1980

[51] Int. Cl.³ .............................................. C12P 19/38
[52] U.S. Cl. ...................................... 435/87; 435/88; 435/72; 424/180

[58] Field of Search .................... 435/88, 92, 87, 89

[56] References Cited

U.S. PATENT DOCUMENTS 3,269,917  8/1966  Imada et al. .......................... 435/88

Primary Examiner—Alvin E. Tanenholtz
Attorney, Agent, or Firm—Donald Brown

[57] ABSTRACT

4-Substituted-3-deazapurine ribosides are prepared by the enzymatically catalyzed reaction of 4-substituted-3-deazapurine with a ribose donor.

9 Claims, No Drawings

SYNTHESIS OF RIBOSIDES USING BACTERIAL PHOSPHORYLASE

The present invention relates to the preparation of imidazo(4,5-c)pyridine derivatives. More specifically the invention is concerned with the preparation of 4-substituted-1-B-D-ribosyl imidazo-(4,5-c)pyridines.

4-Substituted-1-B-D-ribosyl imidazo-(4,5-c)pyridines (I)

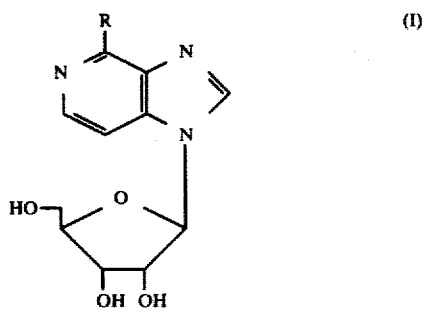

are of interest as compounds of pharmacological interest and/or as intermediates thereto. For example 3-deazaadenosine, 4-amino-1-B-D-ribofuranosyl-1H-imidazo(4,5-c)pyridine ((I), R=NH$_2$) has generated considerable interest as a compound of biological potential (see for example P. K. Chiang et al., *Molec. Pharm.* 1977, 13, 939–947). In particular 3-deazaadenosine has been taught as an antifocal and antifungal agent (U.S. Pat. No. 4,148,888) and an immunosuppressant (European Patent Application No. 79103947.2).

4-Chloro-1-B-D-ribofuranosyl-1H-imidazo-(4,5-c)pyridine ((I)R=Cl) is a key intermediate in the preparation of a number of compounds of formula (I), including the 4-amino derivative referred to above, as described for example by:

Mizuno et al., *Chem. Pharm. Bull.* (Tokyo) 1968, 16, 2011;
Montogomery & Townsend, *J. Med. Chem.* 1966, 9, 105; and
Rosseau et al., *Biochemistry* 1966, 5, 756.

Other compounds of formula (I) of interest include for example the 4-mercapto and 4-thiomethyl derivatives (Montgomery & Townsend, supra.)

The potential of these 4-substituted-1-B-D-ribofuranosyl-1H-imidazo-(4,5-c)pyridines has been limited, however, by reason that they are not readily prepared. The usual route is ribosylation by conventional organic chemical means of selected intermediates, in particular the 4-chloro derivative ((I), R=Cl) followed where necessary by modification of the substituent at the 4-position.

However, the yields of the ribosylation step have been relatively low (30–40%) and the reactions used are well known to be stereochemically non-specific leading to products of doubtful stereochemistry and requiring extensive purification procedures. In addition, the nature of these chemical reactions is such that they are not readily adaptable to a large scale production.

Attempts have been made to provide improved syntheses of these 4-substituted compounds in particular the 4-amino compound for example that described by May and Townsend, *J.C.S. Chem. Commun.*, 1973, 64 where the ribosylation was carried out on 4,6-dichloro-1H-imidazo(4,5-c)pyridine. Whilst this improved the yield of the ribosylation step to about 46%, it suffered from the disadvantages that the intermediate (III) is less readily accessible and that the product obtained from the ribosylation step requires additional steps to convert it to compounds of formula (I). This method, being chemical, also suffers from the disadvantages inherent in such a method and referred to above.

The problem of the preparation of purine nucleosides by chemical means is generally recognised and with certain purine bases this has been overcome by means of an enzymatic pentosylation (see for example European Patent Application No. 78101295.0), a purine nucleoside phosphorylase being used as the essential catalyst.

It is well known that enzymes have a high degree of specificity and that small changes in the substrate(s) may markedly affect the enzyme's ability to catalyse a reaction. It has been reported that modification of the purine base by removal of or addition to the heterocyclic ring system of a nitrogen atom affects the ability of the base to act as a substrate for purine nucleoside phosphorylases. Thus a number of 3-deazapurines have been shown not to be substrates for mammalian purine nucleoside phosphorylase (Townsend et. al., Lectures in Heterocyclic Chemistry Vol. 4, supplement to *J. Hetero. Chem.* 1978, 15, S-19 to S-95) and 7-deazaadenosine, 7-deazainosine and 8-azaguanosine have been shown not to be substrates for microbial purine nucleoside phosphorylase (Doskocil and Holy, *Coll. Czeck. Chem. Commun.*, 1977, 42, 370–383). Further it has been shown that 3-deazapurine nucleosides have conformations which differ from their purine counterparts (Ludemann et. al., *A. Naturforsch,* 1978, 33C, 305–316; May et. al., *J. Amer. Chem. Soc.,* 1976, 98, 825–830) suggesting that purines and 3-deazapurines may be expected to behave differently in the relevant enzyme systems.

We have now surprisingly found that 4-substituted 1H-imidazo-(4,5-c) pyridines may be readily ribosylated by an enzymatic method, with the advantages over the prior art chemical methods that it is stereospecific, adaptable to large scale production and offers improved yield in the ribosylation reaction.

The present invention accordingly provides a method for preparation of 4-substituted-1-B-D-ribofuranosyl-1H-imidazo(4,5-c)pyridines which method comprises the reaction of a 4-substituted-1H-imidazo(4,5-c)pyridine with a ribose donor system comprising ribose-1-phosphate and a phosphorylase type enzyme.

The 4-substituent may be any substituent required in the final product the chemical nature of the substituent having little effect in the case of the ribosylation, in contrast to the chemical methods of the prior art where the nature of the 4-substituent may be critical to the course of the ribosylation reaction. Of particular interest are halogens, amino, thiol, alkylthio, substituted amino (including lower alkyl amino and protected amino such as benzyl amino and benzhydryl amino) substituents.

Of the compounds of the formula (I), 4-amino-1-B-D-ribofuranosyl-1H-imidazo(4,5-c)pyridine (R=NH$_2$) is a compound of particular interest and may be prepared directly by ribosylation of 4-amino-1H-imidazo(4,5-c)pyridine, a method not practicable by the prior art chemical means.

Alternatively the 4-amino compound may be prepared by ribosylation of compounds in which the 4-amino group is protected by a blocking group such as benzyl or benzhydryl followed by removal of the blocking group by conventional means, including reduction using Raney Nichel, metallic sodium in liquid ammonia, or hydrogen gas and an appropriate catalyst.

In a further alternative the 4-amino compound may be prepared by modification of the ribosylation step of prior art methods. Such methods involve ribosylation of 4-chloro-1H-imidazo(4,5-c)pyridine followed by the conversion of the chloro group to an amino group. This conversion may be carried out by prior art methods such as direct amination, or by conversion to the 4-hydrazino derivative followed by hydrogenation to give the 4-amino compound. Alternatively the chloro compound may be converted to a protected amino group for example benzyl amino or benzhydrylamino and the blocking group removed by conventional methods, for example those described above.

The invention accordingly provides in a further aspect a method for the preparation of 4-amino-1-B-D-ribofuranosyl-1H-imidazo(4,5-c)pyridine which comprises enzymatic ribosylation of a compound of formula (I) wherein R is halogen or a protected amino group by the method described above followed conversion of the 4-substituent to an amino group.

Although the ribose-1-phosphate required for the invention described herein may be provided by synthetic processes known in themselves in the literature (Wright, R. S. and Khorana, H. G., *J. Am. Chem. Soc.*, 78, 811 (1956), it can be convenient or even advantageous if the same is generated enzymatically in situ from a ribosyl donor and an inorganic phosphate to obtain the required ribose-1-phosphate. Although the reactions may be carried out separately, that is by isolating the ribose-1-phosphate from an enzymatic reaction or chemically synthesizing ribose-1-phosphate and using it as a starting material, it has been found advantageous to carry out both reactions in a "one pot" process by forming the ribose-1-phosphate intermediate in situ. The net effect of the coupled reactions therefore is the transfer of the ribosyl moiety of the donor ribonucleoside to the free 3-deazapurine base, thereby producing the desired ribonucleoside.

The ribosyl moiety donor may be a purine ribonucleoside for example, adenosine, a pyrimidine ribonucleoside, for example uracil ribonucleoside, or a mixture of various ribonucleoside and non-nucleoside material. However, for the purpose of the present invention it is preferable that the ribosyl moiety donor is substantially free from non-nucleoside material and also that it is a pyrimidine ribonucleoside.

The reasons for the preference for the use of a pyrimidine ribonucleoside as the donor are two-fold. Firstly, the properties of the donor ribonucleoside are sufficiently different from those of the desired product to facilitate easy purification. Secondly, the donor base liberated during the course of the reaction is a pyrimidine rather than a purine which results is substantially less competition between the donor base and the acceptor base for the catalytic site on the enzyme directly involved in product synthesis (purine nucleoside phosphorylase).

The pyrimidine ribonucleoside donors and purine nucleoside donors may be prepared by any of the methods known in the art, for instance, according to the procedure described by Hotchiss, R. D. *J. Biol. Chem.*, 175, 315 (1948).

It has been found that both reactions described hereinabove are catalysed by various enzymes which are present in many different microorganisms and mammalian tissues. The phosphorolysis of the donor ribonucleoside is catalysed, for instance, by purine nucleoside phosphorylase if the donor is a purine ribonucleoside, or by pyrimidine nucleoside phosphorylase, thymidine phosphorylase or uridine phosphorylase if the donor is a pyrimidine ribonucleoside. The second reaction, by which the desired 3-deazapurine ribonucleoside is synthesized from the 3-deazapurine and ribose-1-phosphate, is catalysed by purine nucleoside phosphorylase.

The required ribosyl transferring enzyme system therefore may consist of the latter phosphorylase alone, or in combination with any one of the former type, if the ribosyl donor is a ribonucleoside of a pyrimidine or pyrimidine analogue.

As previously stated, it has been found that the enzymes required for the catalysis of the reactions employed in the process of the present invention occur in many different microorganisms as well as mammalian tissues. For the purposes of the present invention, however, aerobic bacteria such as *B. stearothermophilus* and especially *E. coli* B, which is freely available from the American type culture collection under deposition No. ATCC 11303, were found to be excellent sources of such enzymes. The bacteria which provide the enzymes may be cultured under a variety of conditions. However, media which contained large quantities of glucose were found to be undesirable since the levels of the nucleoside phosphorylase enzymes in the bacterial cells were depressed in the presence of glucose.

It has been found that crude enzyme preparations are less suitable than purified preparations. This is due to the fact that crude preparations contain troublesome nucleic acids as well as enzymes other than those required for the process of the present invention. The extraneous enzymes in crude preparations catalyse undesirable alterations of substrates and products, and may even cause proteolysis of the required enzymes themselves. These factors decrease not only the yield of the desired products but also the ease with which they can be isolated from reaction mixtures.

In most cases therefore, it is desirable to purify the crude enzyme preparations before addition to the reaction mixture. This may be achieved in a number of ways known in themselves in the art. For instance, the desired enzymes may be separated or concentrated from extracts of the cells by a combination of treatment with calcium phosphate gel and ion exchange chromatography. Alternatively the cell extract may be treated with streptomycin or nuclease (DNA ase+RNA ase) prior to calcium phosphate gel treatment or by nuclease (DNA ase+RNA ase) treatment prior to ion exchange chromatography. Nuclease treatment is particularly advantageous if performed under dialyzing conditions at 4° to 40° C., preferably at 25° C. Gel filtration has been found especially useful as a late or final step in the purification when only relatively small volumes of liquid are involved.

The enzymes, provided in a sufficiently effective state and concentration, may then be used to catalyse the aforementioned reactions. A typical reaction mixture contains a ribosyl donor, a 3-deazapurine base, inorganic phosphate, for example dipotassium hydrogen phosphate ($K_2HPO_4$), and the appropriate enzyme or enzymes in an aqueous medium or in a medium containing up to 50% of an organic solvent such as methanol, ethanol, propanol, butanol, acetone, methylethylketone, ethyl acetate, toluene, tetrahydrofuran, dioxane, dimethyl sulfoxide, trichloromethane, or cellosolve. The preferred concentration can be from 0.001 mM to 2,000 mM, preferably 1 to 200 mM.

The reaction is performed at near neutral pH, that is, in the pH range of about 5 to 9, preferably 6.0 to 8.5 and at a temperature of 3° to 70° C. Mild conditions are preferably since the glycosidic bond of purine ribonucleosides is liable under acid conditions, particularly at elevated temperatures, and the enzymes are unstable at extremes of temperatures and pH. The preferable concentration of the enzymes is a function of the substrate efficiency of the particular ribosyl donors and acceptors used and the length of time that one wishes to allow the reaction to proceed. In some cases it is preferable to use larger amounts of the enzyme in order to reduce the reaction time because of the instability of certain of the products in aqueous solution. The purity of the enzymes used is a question of convenience. Crude extracts will catalyze the desired reactions but the yield of product is usually less and its isolation is more difficult than when purified enzymes are used for the reasons explained above. If the enzymes used are stored as ammonium sulfate suspensions, they are preferably added to the reactions as centrifuged pellets from the suspensions rather than as the whole suspensions.

Enzymes may be salvaged from reaction mixtures, for instance by batch adsorption onto DEAE-cellulose after the reaction has reached a satisfactory point and subsequent removal from the soluble components of the reaction mixture by centrifugation or by gel filtration of reaction mixtures. In some cases, enzymes may be recycled by virtue of the fact that the bulk of the product precipitates out from the reaction mixture and, upon its removal, more starting material may be added to the reaction fluid in order that the product formation may be resumed.

Usually it is preferable that all the components are contained in suspension or solution but when highly soluble substrates are used an alternative procedure wherein a solution of the reaction mixture components except enzymes is pumped slowly through a column containing a stationary phase to which the appropriate enzymes have been fixed, (for instance, when the enzymes are adsorbed on a DEAE-cellulose) may be preferable.

It has been found that, if it is so desired, enzymes may be conserved by allowing reactions to proceed for extended periods of time, for example, up to thirty days or longer. However, for reaction mixtures which are incubated for more than one day it is desirable to have an antimicrobial agent, for example sodium or potassium azide or toluene, in the reaction mixture, unless the reaction mixture is sterilised by filtration or some other technique known to the art.

The desired purine ribonucleosides may be recovered or isolated by any of the known means for separating mixtures of chemical compounds into individual compounds. For example, the separation can be affected by utilizing differences in the solubilities in various solvents between the desired end product and impurities, the difference in their distribution coefficients between two solvent layers, the difference in their adsorbabilities to an adsorbent such as ion-exchange resins, the difference in their rates of passage through crosslinked resins such as polyacrylamide gels, or the difference in their crystallizabilities from a solvent. In cases where the product crystallizes out of the reaction mixture, it can be collected by centrifugation or by filtration with or without a filter aid. In practice, these means for separation or isolation are carried out in combination or repeatedly depending on the desired purity and state of the products.

The following Examples illustrate the invention but should in no way be considered as a limitation thereof.

EXAMPLE 1

Preparation of 4-Amino-1-B-D-ribofuranosyl-1H-imidazo(4,5-c)pyridine

A reaction mixture comprising an aqueous suspension (30 ml) containing 4-amino-1H-imidazo(4,5-c)pyridine (2.4 m moles), uridine (7.2 m moles), $K_2HPO_4$ (2.8 m moles), potassium azide (0.14 m moles), purine nucleoside phosphorylase (1, 120 International Units IU), (obtained as described in European Patent Application No. 78101295.0) and uridine phosphorylase (156 IU) purified from *Escherichia coli* (Krenitsky, T. A., *Biochim. Biophys. Acta*, 1976, 429, 352–358) was prepared, the pH of the reaction mixture being adjusted to 7.0 with potassium hydroxide prior to addition of the enzymes. After 15 days at 37° C., the reaction mixture was filtered and then clarified by centrifugation at 48,000 × g at 3° C. for 10 minutes. The supernatant was applied to a Sephadex G-10 column (2 × 90 cm). The column was eluted with water. Fractions containing product (monitored by TLC/$H_2O$) were combined and the volume reduced in vacuo to 40 ml. n-Propanol (20 ml) was added to the solution. After clarification by filtration, the solution was applied to a column packed with polyacrylamide (P-2, Bio Rad Laboratories) (5 × 90 cm) and the eluted with 30% n-propanol. After elution with 3 liters of 30% n-propanol, 50 ml of a saturated solution of ammonium bicarbonate in 30% n-propanol was applied to the column and then elution with 30% n-propanol was resumed. Product was eluted and dried in vacuo. The dried material was dissolved in water (5 ml) and applied to a Sephadex G-10 column (2 × 90 cm) and eluted with water. Fractions containing the product were pooled and lyophilized, to give 4-amino-1-B-D-ribofuranosyl-1H-imidazo(4,5-c)pyridine as the hemihydrate.

Anal. calculated for $C_{11}H_{14}N_4O_4 \cdot \frac{1}{2}H_2O$: Theory: C, 48.00; H, 5.49; N, 20.35%. Found: C, 48.05; H, 5.51; N, 20.40%.

| U.V. Spectra (nm) | Max | Min | Shoulder |
|---|---|---|---|
| 0.1N HCl | 262 | 230 | 275 |
| 0.1N NaOH | 265.5 | 232 | |

Thin layer chromatography (TLC): a chromatograph on cellulose using water as the solvent showed only a single spot.

EXAMPLE 2

4-Chloro-1-B-D-ribofuranosyl-1H-imidazo(4,5-c)pyridine

A reaction mixture was prepared comprising 4-chloro-1H-imidazo (4,5-c)pyridine (23 m moles), uridine (27.4 m moles), potassium phosphate (11 m moles), water (123 ml), n-propanol (20 ml), purine nucleoside phosphorylase (as described in Example 1, 13,000 I.U.) and uridine phosphorylase (as described in Example 1, 1,100 I.U.). Prior to addition of the enzymes the pH of the reaction mixture was adjusted to 6.7. The suspension was incubated at 37° C. for 11 days and then further purine nucleoside phosphorylase (1,000 I.U.) and of uridine phosphorylase(100 I.U.) added. After 2 more days at 37° C., the reaction mixture was filtered and the filtrate placed on a rotary evaporator until the volume was decreased by one half. After a second filtrate was applied to a Sephadex column (G-10) (5×90 cm) and eluted with water. Fractions containing the product were combined and evaporated to 10 ml in vacuo. This solution was applied to a column packed with polyacrylamide (P-2, Bio Rad Laboratories) (2.5×90 cm) and eluted with 30% n-propanol. Fractions containing the product without yellow colour were combined and evaporated in vacuo until the bulk of the propanol was removed. The remaining water was removed by lyophilization to give 4-chloro-1-B-D-ribofuranosyl-1H-imidazo(4,5-c)pyridine (2.9. g).

Anal. Calculated for $C_{11}H_{12}ClN_3O_3$: Theory: C, 46.24; H, 4.23; N, 14.70 Cl, 12.41%. Found: C, 46.32; H, 4.26; N, 14.66; Cl, 12.38%.

| Solvent | U.V. Spectra (nm): | | |
|---|---|---|---|
| | Max | Min | Shoulder |
| 0.1N HCl | 257,266 | 236 | 273 |
| 0.1N NaOH | 274 | 235 | 260,269 |

Thin layer chromatography: A chromatograph on cellulose using n-propanol/saturated aqueous ammonium sulphate/N sodium acetate (2:79:19) as solvent, gave a single spot.

EXAMPLE 3

Preparation of
4-Amino-1-B-D-ribofuranosyl-1H-imidazo(4,5-c)pyridine from the 4-chloro analogue (a) via the 4-hydrazino intermediate A solution of 4-chloro-1-B-D-ribofuranosyl-1H-imidazo(4,5-c)pyridine (1 g, 3.5 m mole) (Example 2) in 40 ml hydrazine hydrate was heated at reflux in a nitrogen atmosphere for 1 hour. The solution was taken to dryness in vacuo and the residue was dissolved in deoxygenated water (80 ml). After Raney Nickel (3.8 net weight) was added, the mixture was refluxed for 1 hour and then filtered through a bed of celite and the catalyst was washed well in boiling water. The filtrate and washings were taken to dryness in vacuo, redissolved in water (30 ml) and ammonium sulfide solution (1 ml) was added. After standing overnight a precipitate formed. It was removed by filtration in vacuo and the solution was lyophilized. The coloured material was dissolved in water and chromatographed on cellulose using water as the eluant. The fractions containing product were pooled and taken to dryness in vacuo. The residue was chromatographed on silica gel in chloroform/methanol mixtures. The appropriate fractions were combined, taken to dryness and methanol was added to the residue. The solid which resulted (0.51 g) was dissolved in water and treated with gaseous hydrogen sulfide. The precipitate which formed upon standing was removed by filtration and the filtrate was lyophilized. The residue was dissolved in water and applied to a column containing Dowex-50-H+. After a thorough water wash, the material was eluted with 0.5 N ammonium hydroxide solution. The fractions were combined, taken to dryness in vacuo and the residue was crystallized from water to give 4-amino-1-B-D-ribofuranosyl-1H-imidazo(4,5-c)pyridine (0.23 g, 0.86 m mole, 25%).

Anal. calculated for $C_{11}H_{14}N_4O_4$: Theory: C, 49.62%; H, 5.30%; N, 21.04%. Found: C, 49.36%; H, 5.12%; N, 21.01%.

(b) via the 4-benzyl intermediate

4-Chloro-1-B-D-ribofuranosyl-1H-imidazo(4,5-c)pyridine (28.57 g), and benzylamine (26.75 g) were refluxed in 2-ethoxyethanol (142) ml under a nitrogen atmosphere for 18 hours. The reaction mixture was evaporated to dryness and the residue recryallised twice from SD3A-water (1:1 v/v), to give 4-benzylamino-1-B-D-ribofuranosyl imidazo (4,5-c)pyridine (28.23 g).

The thus obtained 4-benzylamino intermediate (28.1 g) was dissolved in warm 2-methoxyethanol (350 ml) and 20% palladium hydroxide on carbon catalyst (PD(OH)/2C, 5 g), suspended in 2-methoxyethanol, added to the solution. The resulting reaction mixture was hydrogenolysed at slightly above atmospheric pressure at about 55° C. for 3 days. The reaction mixture was filtered and concentrated to dryness and the residue stirred in hot water (600 ml), cooled at 20° C. and filtered. The filtrate was exhaustively extracted with ethyl acetate, the extracts discarded and the filtrate concentrated to about 100 ml and cooled to give the desired product which was collected by filtration. A second crop was obtained by adjusting the filtrate to pH 10 and further concentrating the solution. The second crop was recrystallised from water, combined with first crop and the combined crops recrystallised from SD3A-water (2:1 v/v; 200 ml) to give 4-amino-1-B-D-ribofuranosyl-1H-imidazo(4,5-c)pyridine (12.5 g).

EXAMPLE 4

4-Benzylamino-1-B-D-ribofuranosyl-1H-imidazo(4,5-c)pyridine (a) Preparation of
4-Benzylamino-1H-imidazo(4,5-c)pyridine A mixture of chloro-1H-imidazo(4,5-c)pyridine (2.0 g, 13 mmol), benzylamine (5 ml) and a few drops of water was heated at reflux for 4 days. The reaction mixture was poured onto ice and water and the cold mixture was extracted twice with diethyl ether. The ether was removed in vacuo and the residual oil was triturated twice with hexane. The oil was suspended in water and the aqueous phase was neutralised with glacial acetic acid. The aqueous phase was taken to dryness in vacuo and resuspended in water (15 ml) and applied to a column of Dowex 50 (H+) resin (10 g). The column was washed with water until the ultra violet absorbance of the eluant was zero. The column packing was removed from the column and heated with several portions of concentrated ammonium hydroxide solution (400 ml). The basic solution was filtered in vacuo, cooled and neutralized with glacial acetic acid. The yellow solid was collected and dried in vacuo at 40° C. to give 4-benzylamino-1H-imidazo(4,5-c)pyridine 0.94 g, m.p. 60°-64° C., 31.5%.

Analysis calculated for $C_{13}H_{12}N_4O.3H_2O$: Theory: C: 67.88; H: 5.53; N: 24.40%. Found: C: 68.05; H: 5.26; N: 24.23%.

| Solvent | UV Data: | | |
|---|---|---|---|
| | Max (nm) | E | Shoulder |
| 0.1N HCl | 277 | 13000 | 263 |

| UV Data: | | | |
|---|---|---|---|
| Solvent | Max (nm) | E | Shoulder |
| 0.1N NaOH | 278 | 11900 | |

(b) Preparation of
4-Benzylamino-1B-D-ribofuranosyl-1H-imidazo(4,5-c)pyridine

A reaction mixture was prepared comprising uridine (4.1 g) 4-benzylamino-1H-imidazo(4,5-c)pyridine (0.68 g) (prepared as in Example 4a), 0.2 M Kx Hy PO4 (pH 7.4) (6 ml), 0.13 mM Na2 EDTA (6 ml), water (200 ml) n-propanol (10 ml), purine nucleoside phosphorylase (as described in Example 1, 2,800 I.U.) and uridine phosphorylase (as described in Example 1, 390 I.U.). This so obtained suspension was incubated at 37° C. and for 4 days. The so obtained suspension was filtered and the filter cake washed with water and dried in vacuo to give 4-benzylamino-1B-D-ribofuranosyl-1H-imidazo(4,5-c)pyridine (0.39 g) as the monohydrate.

A second crop of crystals, obtained by cooling the filtrate to 3° C., which was washed and dried in vacuo, to give a total yield of 0.43 g of product.

Analysis calculated for $C_{18}H_{20}N_4O_4 \cdot H_2O$: Theory: C, 57.74; H, 5.92; N, 14.96%. 1st crop Found: C, 57.54; H, 5.94; N, 14.98%. 2nd crop Found: C, 57.45; H, 5.96%; N, 14.95%.

| | U.V. spectrum (nm) | |
|---|---|---|
| Solvent | λMax | λMin |
| 0.1N HCl | 268 | 236 |
| 0.1N NaOH | 273.5 | 238 |

What we may claim comprise any novel feature disclosed herein, principally, but not exclusively, for example:

(i) Method for preparation of 4-substituted-1-B-D-ribofuranosyl-1H-imidazo(4,5-c)pyridine comprisings the reaction of a 4-substituted-1H-imidazo(4,5-c)pyridine with a ribose donor system comprising ribose-1-phosphate and a phosphorylase type enzyme.

(ii) An improved process for the preparation of 4-amino-1-B-D-ribofuranosyl-1H-imidazo(4,5-c)pyridine which comprises ribosylating a 4-halogeno-1H-imidazo(4,5-c)pyridine followed by conversion of the halogeno substituent to an amino group, characterised in that ribosylation is carried out enzymatically by reaction with ribose-1-phosphate and a phosphorylase type enzyme.

(iii) 4-Substituted-1-B-D-ribofuranosyl-1H-imidazo(4,5-c)pyridines whenever prepared by the process defined in (i) or (ii) above.

We claim:

1. A method for the preparation of 4-substituted-1-B-D-ribofuranosyl-1H-imidazo(4,5-c)pyridines which method comprises the reaction of the corresponding 4-substituted-1H-imidazo(4,5-c)pyridine with a ribose donor system comprising ribose-1-phosphate and bacterial phosphorylase enzyme.

2. A method according to claim 1 wherein the 4-substituent is selected from hydrogen, halogen, amino, loweralkylamino, aralkylamino, thio, or thio(lower) alkyl.

3. A method according to claim 1 wherein the phosphorylase enzyme comprises at least one purine nucleoside phosphorylase.

4. A method according to claim 1 wherein the ribose-1-phosphate is generated in situ from a ribosyl donor and an inorganic phosphate.

5. A method according to claim 4 wherein the ribosyl donor is selected from a purine nucleoside, a pyrimidine nucleoside or a mixture thereof, or a mixture thereof with non-nucleoside material.

6. A method according to claim 5 wherein a purine nucleoside phosphorylase or a pyrimidine nucleoside phosphorylase is used in the enzymatic generation of ribose-1-phosphate.

7. A method according to claim 6 wherein the enzyme or enzymes are obtained from B stearothermophilus or E.coli, B strain, ATCC 11303.

8. In a method for the preparation of 4-amino-1-B-D-ribofuranosyl-1H-imidazo(4,5-c)pyridine which comprises the ribosylation of a 4-halogeno-1H-imidazo(4,5-c)pyridine followed by conversion of the halogen to an amino group, the improvement wherein the ribosylation is carried out enzymatically by reaction with a ribose donor system comprising ribose-1-phosphate and bacterial phosphorylase enzyme.

9. The method of claim 1 in which 3-deazaadenosine is prepared.

* * * * *